United States Patent
Dias

(10) Patent No.: US 9,763,885 B2
(45) Date of Patent: Sep. 19, 2017

(54) ORAL TABLET FORMULATION CONSISTING OF FIXED COMBINATION OF ROSUVASTATIN AND EZETIMIBE FOR TREATMENT OF HYPERLIPIDEMIA AND CARDIOVASCULAR DISEASES

(71) Applicant: Althera Laboratories Ltd., Dublin (IE)

(72) Inventor: Marie Charmaine Dias, Morristown, NJ (US)

(73) Assignee: Althera Laboratories Ltd., Dublin (IE)

( * ) Notice: Subject to any disclaimer, the term of this patent is extended or adjusted under 35 U.S.C. 154(b) by 0 days.

(21) Appl. No.: 14/350,905

(22) PCT Filed: May 1, 2013

(86) PCT No.: PCT/US2013/039018
§ 371 (c)(1),
(2) Date: Apr. 10, 2014

(87) PCT Pub. No.: WO2013/166117
PCT Pub. Date: Nov. 7, 2013

(65) Prior Publication Data
US 2014/0287042 A1    Sep. 25, 2014

Related U.S. Application Data

(60) Provisional application No. 61/641,013, filed on May 1, 2012.

(51) Int. Cl.
*A61K 9/00* (2006.01)
*A61K 9/20* (2006.01)
*A61K 31/397* (2006.01)
*A61K 31/505* (2006.01)
*A61K 9/24* (2006.01)

(52) U.S. Cl.
CPC .......... *A61K 9/2086* (2013.01); *A61K 9/2009* (2013.01); *A61K 9/209* (2013.01); *A61K 9/2018* (2013.01); *A61K 9/2027* (2013.01); *A61K 9/2054* (2013.01); *A61K 31/397* (2013.01); *A61K 31/505* (2013.01)

(58) Field of Classification Search
CPC .............. A61K 2300/00; A61K 31/397; A61K 31/505; A61K 9/2009; A61K 9/2018; A61K 9/2027; A61K 9/2054; A61K 9/2086; A61K 9/209
See application file for complete search history.

(56) References Cited

U.S. PATENT DOCUMENTS

| | | | |
|---|---|---|---|
| 2003/0072800 A1 | 4/2003 | Singh et al. | |
| 2004/0126423 A1* | 7/2004 | Moore et al. | 424/465 |
| 2010/0204195 A1* | 8/2010 | Lulla et al. | 514/210.02 |
| 2010/0247645 A1* | 9/2010 | Curdy et al. | 424/468 |
| 2011/0262497 A1* | 10/2011 | Injac et al. | 424/400 |

FOREIGN PATENT DOCUMENTS

| | | | |
|---|---|---|---|
| EP | 2233133 A1 * | 9/2010 | |
| WO | 2009/024889 A2 | 2/2009 | |
| WO | WO 2009024889 A2 * | 2/2009 | |
| WO | 2010/021608 A1 | 2/2010 | |
| WO | 2011/019326 A2 | 2/2011 | |
| WO | 2011/139256 A2 | 11/2011 | |
| WO | 2011/139256 A3 | 11/2011 | |
| WO | 2012/064307 A1 | 5/2012 | |
| WO | WO 2013066279 A1 * | 5/2013 | |

OTHER PUBLICATIONS

PCT International Search Report and Written Opinion, Sep. 20, 2013.
PCT Notification Concerning Transmittal of International Preliminary report on Patentability, Nov. 13, 2014.
European Patent Office Supplementary European Search Report for EP13785009.5 dated Nov. 27, 2015.

* cited by examiner

*Primary Examiner* — Robert A Wax
*Assistant Examiner* — Olga V Tcherkasskaya
(74) *Attorney, Agent, or Firm* — Berggren, Inc.

(57) ABSTRACT

The present invention is an orally consumed fixed combination formulation of both rosuvastatin and ezetimibe in one tablet that is expected to have the same Area Under Curve as two active ingredients taken together individually orally, and pharmaceutically acceptable additives suitable for the preparation. In preferred embodiments of this invention, the rosuvastatin is in the form of rosuvastatin calcium and the pharmaceutically acceptable additives are selected from diluents, disintegrants, glidants, lubricants, colorants and combinations thereof.

9 Claims, 1 Drawing Sheet

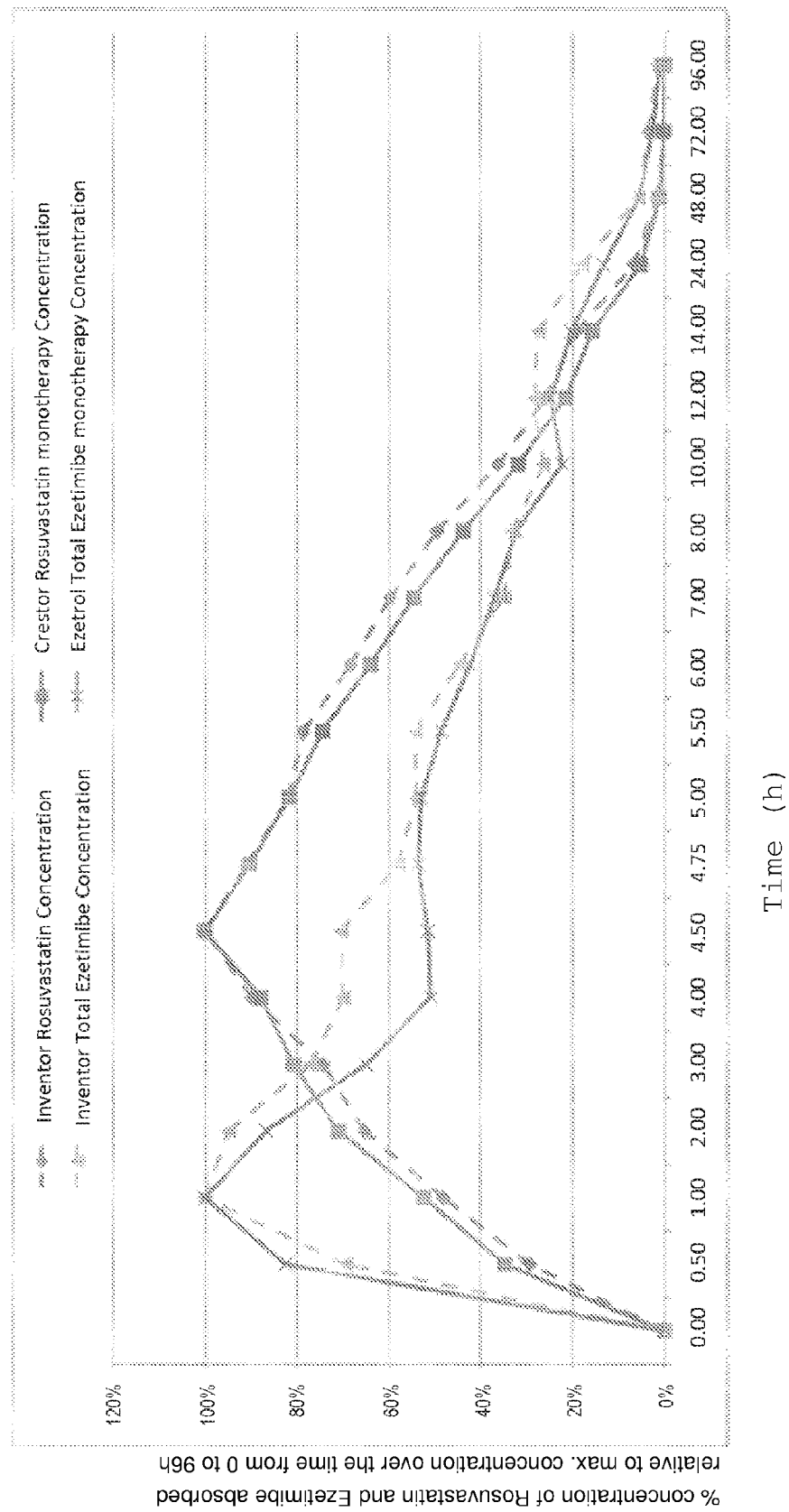

ORAL TABLET FORMULATION CONSISTING OF FIXED COMBINATION OF ROSUVASTATIN AND EZETIMIBE FOR TREATMENT OF HYPERLIPIDEMIA AND CARDIOVASCULAR DISEASES

PRIORITY

This application is a national entry of PCT/US2013/039018 filed on May 1, 2013, claiming priority of U.S. Provisional application Ser. No. 61/641,013 filed on May 1, 2012, both of which are fully incorporated herein by reference.

BACKGROUND OF THE INVENTION

1. Field of invention

The present invention is directed to solid dosage formulations containing a combination of rosuvastatin and ezetimibe, as well as to methods of making such solid dosage forms and method of treating patients with fixed combination solid dosage forms of rosuvastatin and ezetimibe.

2. Related background Art

Cardiovascular disease is one of the largest causes of death in the US, Europe, and also developing nations such as Brazil, Mexico, Russia, China, Turkey and India. Throughout the WHO (World Health Organization)_European Region, cardiovascular disease is estimated to account for more than 5 million deaths as well as almost one-quarter of the region's disease burden; WHO estimates 8.7% of the total disease burden in Europe is due to high blood cholesterol, and presence of high levels of Low Density lipids (LDL). Rosuvastatin is an inhibitor of 3-hydroxy-3-methylglutaryl coenzyme A (HMG CoA reductase inhibitor) that works by inhibiting the enzyme HMG CoA reductase; HMG CoA is one of the key regulators of cholesterol synthesis in the liver and blockade of the enzyme leads to substantial reduction in total cholesterol (TC), low density lipoprotein cholesterol (LDL-C) and very low density lipoprotein cholesterol (VLDL-C). Ezetimibe is a compound that also reduces TC and LDL-C but by a different mechanism as it binds cholesterol in the intestine, thereby reducing intestinal absorption of cholesterol. The rosuvastatin and ezetimibe molecules may be selected from any of those disclosed in U.S. Pat. Nos. RE 37,721; 5,260,440; 5,688,990; 5,656,624; 5,624,920; 5,698,548; 5,627,176; 5,633,246; 5,688,785; 5,688,787; 5,744,467; 5,756,470; 5,767,115 which are incorporated herein by reference.

It has been seen in clinical studies that the patients treated with both rosuvastatin and ezetimibe achieve higher levels of LDL reduction compared to individual therapy of rosuvastatin or ezetimibe alone. Hence there is significant value in a fixed combination of rosuvastatin and ezetimibe if such a formulation can be shown as the same Area Under Curve (AUC) as each of the two components taken together, which is demonstrated in bioequivalence (BE) studies. As used herein, "fixed-combination" refers to a combination of two drugs or active ingredients presented in a single dosage unit such as tablet or a capsule; further as used herein, "free-combination" refers to a combination of two drugs or active ingredients dosed simultaneously but as two dosage units. Such a fixed combination in comparison to individual consumption of the two active ingredients will improve ease of administration, create convenience for the patients that need both the individual drugs and improve compliance in patients who cannot be controlled on either product alone. This formulation, when used will increase the compliance in reduction of LDL and thereby reduce the cardiovascular risk of patients consuming this formulation compared to the monotherapy consumption of either rosuvastatin or ezetimibe alone.

Accordingly, a fixed combination solid dosage formulation of rosuvastatin and ezetimibe that is bioequivalent to corresponding free-combination would be desirable.

SUMMARY OF THE INVENTION

In a first aspect, the present invention is an orally consumed fixed combination formulation of both rosuvastatin and ezetimibe in one tablet that is expected to have the same Area Under Curve as two active ingredients taken together individually orally, and pharmaceutically acceptable additives suitable for the preparation. In preferred embodiments of this invention, the rosuvastatin is in the form of rosuvastatin calcium and the pharmaceutically acceptable additives are selected from diluents, disintegrants, glidants, lubricants, colorants and combinations thereof.

In the preferred embodiments of this invention, the solid dosage form is a bi-layer tablet. The amount of rosuvastatin employed in such bi-layer tablets preferably ranges from 2.5 mg, preferably 5 mg, to 40 mg, including 5 mg, 10 mg and 20 mg. The amount of ezetimibe ranges from 5 mg to 20 mg, preferably 10 mg.

In a second aspect, the present invention leads to creation of a novel formulation that overcomes significant problems encountered during the formulation of combining rosuvastatin and ezetimibe in an oral solid dosage form due to inherent characteristics of rosuvastatin and ezetimibe enumerated as follows: (a) Rosuvastatin calcium is prone to oxidative and moisture mediated degradation both leading to formation of a lactone impurity. This reaction can be arrested in presence of basic milieu, (b) Ezetimibe is practically insoluble in water. While cellulose is the normal excipient that would be used for formulations with rosuvastatin, there is a significant interaction of microcrystalline cellulose with ezetimibe, which makes use of such excipient difficult. Microcrystalline cellulose was found to bind with ezetimibe thereby retarding the drug release from the formulation, which would make it not bioequivalent to individually consumed ezetimibe. (c) While rosuvastatin is more stable in near neutral to alkaline pH, the same is detrimental to ezetimibe. Hence it is important to separate the two individual molecules, which creates a significant product development challenge, (d) Solubility issues of ezetimibe raise the challenge of creating a formulation that achieves the right level of in-vitro dissolution as well as is bioequivalent in a combination form to the individual ezetimibe consumption.

Considering the above challenges, the invention describes a novel approach which separates the two active ingredients—rosuvastatin and ezetimibe in two almost completely separate parts, uses microcrystalline cellulose for the formulation of rosuvastatin, but keeps it separate from ezetimibe and follows a unique process of dissolving ezetimibe and mounting it on lactose to enhance the solubility of ezetimibe when used in combination with rosuvastatin to create a formulation that is bioequivalent and has similar Cmax and area under curve as two individual tablets of rosuvastatin and ezetimibe consumed together. This approach then creates a bi-layer tablet, which has one solid layer of ezetimibe composition and a solid layer of rosuvastatin. This formulation then overcomes the above significant development challenges and enables the Inventor to create a fixed combination formulation that has simultaneously: a) similar dissolution profile to individual active ingredients, which leads to bioequivalence of the two individual active ingredients compared to consumption of two separate tablets of rosuvastatin and ezetimibe, b) a stable formulation despite the incompatibilities of two component molecules—rosuvastatin and ezetimibe, and c) enables the benefit of reducing the cholesterol levels in patients and reducing the cardiovascular risk in patients compared to monotherapies.

In a third aspect, the present invention is directed to a method of making a solid dosage bi-layer form of rosuvastatin and ezetimibe comprising the steps of: (a) blending rosuvastatin calcium with pre-gelatinized starch, calcium hydrogen phosphate, microcrystalline cellulose and crosspovidone, passing through sieve and lubricating the blend with lubricant such as sodium stearyl fumarate to create the rosuvastatin layer blend, (b) mixing ezetimibe with a wetting agent such as sodium lauryl sulphate, and disperse material in sufficient quantity of isopropyl_alcohol and dicholoromethane mixture, (c) absorbing the dispersion on lactose, and mix thoroughly, (d) air drying the dispersion, passing through sieve, mix with croscarmellose sodium, and blend, (e) granulating the mix with polyvinylpyrolidone solution and dry to obtain the ezetimibe granules, (f) creating the desired bi-layer tablet by compressing the two distinctly different set of granules as desired in the second aspect of the invention in a bi-layer compression machine, followed by film coating the oral dosage form.

In a fourth aspect, this invention is directed to solid dosage forms of rosuvastatin and ezetimibe made according to the method of the third aspect.

A fifth aspect of this invention is directed to a method of treating hyperlipidemia, cardiovascular diseases, congestive heart failure, myocardial infarction, atherosclerosis comprising administering a solid dosage form of rosuvastatin and ezetimibe in combination to a patient in need of such a treatment. In a preferred embodiment, the solid dosage form is orally administered to the subject.

DESCRIPTION OF THE FIGURE

FIG. 1.Average Release pattern of Concentration of Rosuvastatin and Ezetimibe when administered to healthy human volunteers, X-Axis depicts time, and Y-axis depicts % concentration of rosuvastatin or ezetimibe absorbed relative to maximum concentration over varying time points from 0 to 96 hours.

DETAILED DESCRIPTION OF THE INVENTION

The present invention relates to solid dosage formulations containing a combination of rosuvastatin and ezetimibe, as well as to methods of making such solid dosage forms and method of treating patients with fixed combination solid dosage forms of rosuvastatin and ezetimibe.

The first embodiment of the invention is a fixed combination orally consumed formulation of both rosuvastatin and ezetimibe in one tablet that is expected to have same Area Under Curve as two active ingredients taken together individually orally, and pharmaceutically acceptable additives suitable for the preparation. In preferred embodiments of this invention, the rosuvastatin is in the form of rosuvastatin calcium and the pharmaceutically acceptable additives are selected from the diluents, disintegrants, glidants, lubricants, colorants and combinations thereof. The preferred solid dosage form is a bi-layer tablet.

Rosuvastatin and ezetimibe suitable for use in the present invention can be purchased from commercial sources or can be prepared according to known methods. Any form of rosuvastatin or ezetimibe may be used for this invention.

The amount of rosuvastatin employed in such bi-layer tablets preferably ranges from 2.5 mg, preferably 10 mg, to 40 mg, including 5 mg, 10 mg and 20 mg. The amount of ezetimibe ranges from 5 mg to 20 mg, and is preferably 10 mg.

In a second embodiment, the present invention leads to a novel formulation that overcomes significant problems encountered during the formulation of combining rosuvastatin and ezetimibe in an oral solid dosage form due to inherent characteristics of rosuvastatin and ezetimibe enumerated as follows: (a) Rosuvastatin calcium is prone to oxidative and moisture mediated degradation both leading to formation of a lactone impurity. This reaction can be arrested in presence of basic milieu, (b) Ezetimibe is practically insoluble in water. While cellulose is the normal excipient that would be used for formulations with rosuvastatin, there is a significant interaction of microcrystalline cellulose with ezetimibe, which makes use of such excipient difficult. Microcrystalline cellulose was found to bind with ezetimibe thereby retarding the drug release from the formulation, which would make it not bioequivalent to individually consumed ezetimibe. (c) While rosuvastatin is more stable in near neutral to alkaline pH, the same is detrimental to ezetimibe. Hence it is important to separate the two individual molecules, which creates a significant product development challenge, (d) Solubility issues of ezetimibe raise the challenge of creating a formulation that achieves the right level of in-vitro dissolution as well as is bioequivalent in a combination form to the individual ezetimibe consumption.

The above challenges were proven by a number of dissolution tests conducted on the formulation described in Table 1, which demonstrates the challenge in creating a formulation that is similar to the individually consumed tablets.

TABLE 1

COMPARATIVE DISSOLUTION PROFILE OF EZETIMIBE IN ROSUVASTATIN 20 mg & EZETIMIBE 10 mg TABLETS

| Appearance of the tablet Formulation details # | White colored round shaped tablets Basket at 75 RPM |
|---|---|
| Time in min/No of tablets | 6 tablets |
| 5 | 45 |
| 10 | 81 |
| 20 | 87 |
| 30 | 89 |
| 45 | 91 |

Considering above challenges, the invention describes a novel approach which separates the two active ingredients—rosuvastatin and ezetimibe in two almost completely separate parts or layers, uses microcrystalline cellulose for the formulation of rosuvastatin, but keeps it separate from ezetimibe and follows a unique process of dissolving ezetimibe and mounting it on lactose to enhance the solubility of ezetimibe when used in combination with rosuvastatin to create a formulation that is bioequivalent and has similar Cmax and area under curve as two individual tablets of rosuvastatin and ezetimibe consumed together. This approach then creates a bi-layer tablet, which has one solid layer of ezetimibe composition and a solid layer of rosuvastatin. This formulation then overcomes the above significant development challenges and enables the Inventor to create a fixed combination formulation that has simultaneously: a) similar dissolution profile to individual active ingredients, which leads to bioequivalence of the two individual active ingredients compared to consumption of two separate tablets of rosuvastatin and ezetimibe, b) a stable formulation despite the incompatibilities of two component molecules—rosuvastatin and ezetimibe, and c) enables the benefit of reducing the cholesterol levels in patients and reducing the cardiovascular risk in patients compared to monotherapies.

In this embodiment, the formulation with the rosuvastatin layer, that is the top layer that consists of rosuvastatin as the active ingredient, with excipients as starch 1-15% of the weight of the rosuvastatin layer, dicalcium phosphate 0.5-10% of the weight of the rosuvastatin layer, Cellulose 20-90% of the weight of the rosuvastatin layer, Crospovidone 2-30% of the weight of the rosuvastatin layer, and lubricants such as sodium stearyl fumarate 0.1-2% of the weight of the rosuvastatin layer. In addition the layer may contain an antioxidant such as butylated hydroxyl anisole 0.05 to 2% of the weight of rosuvastatin layer and a dispersion agent such as Aerosil 1-10% of the rosuvastatin layer. This formulation in a separate layer of rosuvastatin enables a good dissolution of rosuvastatin at the same time avoids the oxidative effects leading to degeneration into lactone, thereby making the rosuvastatin layer more stable while placing the layer on top of the ezetimibe layer.

In this aspect, the formulation with the ezetimibe layer, that is the bottom layer consists of ezetimibe as the active ingredient, with excipients as a surfactant such as sodium lauryl sulphate 2-20% of the ezetimibe layer, lactose 20-90% of the ezetimibe layer, a disintegrant such as croscaramellose 5-30% of the ezetimibe layer, a binder such as polyvinylpyrrolidone 0.5-10% of the ezetimibe layer, and magnesium stearate 0.2-5% of the ezetimibe layer.

METHOD

In a third embodiment, the present invention is directed to a method of making a solid dosage bi-layer form of rosuvastatin and ezetimibe comprising the five steps enumerated below.

(a) Blending rosuvastatin calcium with pre-gelatinized starch, calcium hydrogen phosphate dihydrate, microcrystalline cellulose and crospovidone, passing through sieve and lubricating the blend with lubricant such as sodium stearyl fumarate to create the rosuvastatin layer blend. In the preferred embodiment of this step, rosuvastatin calcium is passed through a sieve, followed by pre-gelatinized starch, calcium hydrogen phosphate dihydrate, microcrystalline cellulose and crospovidone and blended, and then lubricated and blended with sodium stearyl fumarate and passed through another sieve.

(b) Mixing ezetimibe with a wetting agent such as sodium lauryl sulphate, and disperse material in sufficient quantity of Isopropyl alcohol and dicholoromethane mixture. In the preferred embodiment, the mixture is isopropyl alcohol and dicholoromethane. Also in the preferred embodiment, the material of ezetimibe mixed with sodium lauryl sulphate is slowly added to the mixture of isopropyl alcohol and dicholoromethane. This step is important to avoid crystallization of ezetimibe, which may adversely affect dissolution of ezetimibe.

(c) Absorbing the dispersion on lactose, and mix thoroughly. In the preferred embodiment of this step, the solution containing ezetimibe is added to the lactose in a slow process to ensure ezetimibe solution is fully absorbed on lactose, which results on full mounting of ezetimibe on lactose without loss of assay.

(d) Air drying the dispersion, passing through sieve, and mix with croscarmellose sodium and blend. In the preferred embodiment of this step, the ezetimibe solution mounted on lactose is dried evenly at temperatures between 30 degrees Celsius and 55 degrees Celsius. The temperature range avoids crystallization of ezetimibe that can adversely impact the dissolution of ezetimibe granules once process is fully complete. Additionally the ezetimibe mounted on lactose should be air dried rather than oven dried to ensure an even flow of the ezetimbe mounting on lactose.

(e) Mixing with polyvinylpyrolidone solution and dry to obtain the ezetimibe granules. In the preferred embodiment the granules should be dried between 30 and 75 degrees Celsius.

(f) Creating the desired bi-layer tablet by compressing the two distinctly different set of granules as desired in the second aspect of the invention in a bi-layer compression machine, followed by film coating the oral dosage form.

Example 1: fixed combination tablet of rosuvastatin 20 mg and ezetimibe 10 mg

Below is an example of the formulation of a bi-layer tablet with rosuvastatin 20 mg and ezetimibe 10 mg.

| Ingredients | Weight per tablet |
| --- | --- |
| Rosuvastatin | 22.08 |
| Pre-gelatinized starch and dicalcium phosphate | 16.8 |
| Microcrystalline cellulose | 140 |
| Crospovidone, Aerosil and butylated hydroxy anisole (BHA) | 42.1 |
| Total weight of the layer | 220.98 |

| Ingredients | Weight per tablet |
| --- | --- |
| Ezetimibe | 10.08 |
| Sodium lauryl sulphate and croscarmellose | 30 |
| Lactose | 80 |
| Polyvinylpyrrolidone and magnesium stearate | 2.92 |
| Total weight of the layer | 123 |

The method of the above formulation is undertaken in three stages as follows:

Stage A. Rosuvastatin granules: The steps followed to create the rosuvastatin granules are as follows:

1. Pass rosuvastatin through sieve, followed by pre-gelatinized starch, calcium hydrogen phosphate dihydrate, macrocrystalline cellulose and crospovidone through the sieve.

2. Load the Step 1 material blend to Octagonal blender and blend.
3. Pass sodium stearyl fumarate through sieve, load in to Step 2 material and blend.

Stage B. Ezetimibe granules: The steps followed to create the ezetimibe granules are as follows:
1. Pass ezetimibe and sodium lauryl sulphate through sieve and mix.
2. Disperse Step-1 material in quantity sufficient of iso-propyl alcohol and dichloromethane mixture.
3. The prepared Step-2 dispersion adsorb on lactose, mix thoroughly and dried.
4. The Step-3 dried adsorb pass through sieve and mix with previously passed croscarmellose sodium in octagonal blender or suitable container attached to octagonal blender.
5. The Step-4 mixed materials granulate with ⊖ polyvinylpyrrolidone solution and dried.
6. The Step-5 dried granule pass through sieve and the passed granules lubricate with magnesium stearate in octagonal blender or suitable container attached to the blender.

Stage C. Combination of two layers
The rosuvastatin granules and ezetimibe_bed layer granules compressed in bilayer compression machine. Compressed tablet is coated under continuous stirring.

Example 2: fixed combination tablet of rosuvastatin 10 mg and ezetimibe 10 mg

Below is an example of the formulation of a bi-layer tablet with rosuvastatin 10 mg and ezetimibe 10 mg.

| Ingredients | Weight per tablet |
|---|---|
| Rosuvastatin | 11.04 |
| Pre-gelatinized starch and dicalcium phosphate | 8.4 |
| microcrystalline cellulose | 70 |
| Crospovidone, Aerosil and butylated hydroxy anisole (BHA) | 21.05 |
| Total weight of the layer | 110.49 |

| Ingredients | Weight per tablet |
|---|---|
| Ezetimibe | 10.08 |
| Sodium lauryl sulphate and croscarmellose | 30 |
| Lactose | 80 |
| Polyvinylpyrrolidone and magnesium stearate | 2.92 |
| Total weight of the layer | 123 |

The method of the above formulation is undertaken in three stages as follows:

Stage A. Rosuvastatin granules: The steps followed to create the rosuvastatin granules are as follows:
1. Pass rosuvastatin through sieve, followed by pre-gelatinized starch, calcium hydrogen phosphate dihydrate, microcrystalline cellulose and crospovidone through the sieve.
2. Load the Step 1 material blend to Octagonal blender and blend.
3. Pass sodium stearyl fumarate through sieve, load in to Step 2 material and blend.

Stage B. Ezetimibe granules: The steps followed to create the ezetimibe granules are as follows:
1. Pass Ezetimibe and sodium lauryl sulphate through sieve and mix.
2. Disperse Step-1 material in quantity sufficient of isopropyl alcohol and dichloromethane mixture.
3. The prepared Step-2 dispersion adsorb on lactose, mix thoroughly and dried.
4. The Step-3 dried adsorb pass through sieve and mix with previously passed croscarmellose sodium in octagonal blender or suitable container attached to octagonal blender.
5. The Step-4 mixed materials granulate with polyvinylpyrrolidone-solution.
6. The Step-5 dried granule pass through sieve and the passed granules lubricate with magnesium stearate in octagonal blender or suitable container attached to the blender.

Stage C. Combination of two layers
The rosuvastatin granules and ezetimibe bed layer granules compressed in bilayer compression machine. Compressed tablet is coated under continuous stirring.

DISSOLUTION RESULTS

Dissolution is a well established method to test pharmacoequivalence of two products. The pharmacoequivalence of the fixed-combination dosage forms of the present invention was compared with that of the corresponding free-combinations. Table 2 and
Table 3 list the results from the Example described earlier and of multiple tests that were undertaken between the test (fixed-combination) and the reference (free-combination) dosage forms.

TABLE 2

COMPARATIVE DISSOLUTION PROFILE OF CRESTOR 20 MG AND ROSUVASTATIN CALCIUM FROM ROSUVASTATIN 20 mg & EZETIMIBE 10 mg TABLETS

| Time in min | Crestor-20 mg tablets (B. No: HV373) REFERENCE | Rosuvastatin from the Test tablets of Inventor TEST | WITHIN acceptable range to be comparable |
|---|---|---|---|
| 10 | 96 | 84 | YES |
| 20 | 97 | 93 | |
| 30 | 97 | 95 | |
| 45 | 97 | 98 | |

TABLE 3

COMPARATIVE DISSOLUTION PROFILE OF EZETROL 10 MG AND EZETIMIBE FROM ROSUVASTATIN 20 mg & EZETIMIBE 10 mg TABLETS

| Time in min. | Ezetrol 10 mg tablets (B. No: 310688) REFERENCE | Ezetimibe from the test tablets of Inventor TEST | WITHIN acceptable range to be comparable |
|---|---|---|---|
| 10 | 95 | 78 | YES |
| 20 | 95 | 83 | |
| 30 | 95 | 90 | |
| 45 | 95 | 95 | |

STABILITY RESULTS

To test the stability of the formulation, inventors undertook stability test of the formulation. Following are the results of accelerated stability studies of formulations. The tablets were exposed to accelerated stability conditions such as 40° C./75% relative humidity (RH) in unsealed high density polyethylene(HDPE) containers (open condition) for the period of two months. Samples were analyzed each week for degradation products and assay. Summary results are enumerated below in Table 4.

TABLE 4

RELATED SUBSTANCE IMPURITIES FOR ROSUVASTATIN AND EZETIMIBE

| Impurity Name | Limit | 3 weeks 40° C./75% RH | 6 weeks 40° C./75% RH |
|---|---|---|---|
| Rosuvastatin related lactone | Not more than 0.5% | 0.06% | 0.16% |
| Rosuvastatin related keto-impurity | Not more than 0.5% | 0.15% | 0.15% |
| Ezetimibe related cyclic ether impurity | Not more than 0.5% | Not Detected | Not Detected |

The results of above accelerated stability studies depict stabilization potential of the formulation as well as the improved absorption and dissolution of ezetimibe with the novel process.

In a fourth embodiment, this invention is directed to solid dosage forms of rosuvastatin and ezetimibe made according to the method of the third embodiment.

Fifth embodiment of this invention is directed to a method of treating hyperlipidemia, cardiovascular diseases, congestive heart failure, myocardial infarction, atherosclerosis comprising administering a solid dosage form of rosuvastatin and ezetimibe in combination to a patient in need of such a treatment. In a preferred embodiment, the solid dosage form is orally administered to the subject.

While this invention has been particularly shown and described with references to preferred embodiments thereof, it will be understood by those skilled in the art that various changes in form and details may be made therein without departing from the scope of the invention encompassed by the appended claims.

What is claimed is:

1. A solid dosage form comprising rosuvastatin and ezetimibe combined in one bilayer tablet comprising rosuvastatin in a first layer and ezetimibe in a microcrystalline cellulose free second layer, and wherein:
   (i) the solid dosage form when orally administered to healthy individuals is bioequivalent to corresponding dosages of rosuvastatin and ezetimibe taken together individually orally;
   (ii) the solid dosage form comprises rosuvastatin and ezetimibe in a weight ratio of 0.5:1, 1:1 or 2:1, and pharmaceutically acceptable additives suitable for the preparation of solid dosage forms comprising a combination of rosuvastatin and ezetimibe; and wherein rosuvastatin is formulated with microcrystalline cellulose in the first layer and ezetimibe is substantially separated from the microcrystalline cellulose of the first layer; and
   (iii) the said solid dosage form is a stable composition of rosuvastatin and ezetimibe comprising less than 0.5% of ezetimibe related impurities after 6 weeks of storage at 40° C. and 75% relative humidity, less than 0.5% of rosuvastatin related lactone impurities and less than 0.5% of rosuvastatin related keto impurities after 6 weeks of storage at 40° C. and 75% relative humidity.

2. The solid dosage form of claim 1, wherein the rosuvastatin dosage ranges from 2.5 mg to 40 mg, and ezetimibe dosage ranges from 5 mg to 20 mg.

3. The solid dosage form of claim 1 comprising no ezetimibe related impurities after 6 weeks of storage at 40° C. and 75% relative humidity, less than 0.2% of rosuvastatin related lactone impurities and less than 0.2% of rosuvastatin related keto impurities after 6 weeks of storage at 40° C. and 75% relative humidity.

4. The solid dosage form of claim 1, wherein the first layer comprising rosuvastatin as the active ingredient further comprises starch in an amount of 1-15% of the weight of the rosuvastatin comprising first layer, dicalcium phosphate in an amount of 0.5-10% of the weight of the rosuvastatin comprising first layer, microcrystalline cellulose in an amount of 20-90% of the weight of the rosuvastatin comprising first layer, and crospovidone in an amount of 2-30% of the weight of the rosuvastatin comprising first layer as excipients, and sodium stearate fumarate as a lubricant in an amount of 0.1-2% of the weight of the rosuvastatin comprising first layer.

5. The solid dosage form of claim 1, wherein the second layer comprising ezetimibe as the active ingredient further comprises sodium lauryl sulphate in an amount of 2-20% of the weight of the ezetimibe comprising second layer and lactose in an amount of 20-90% of the weight of the ezetimibe comprising second layer, as excipient and surfactant; croscaramellose as a disintegrant in an amount of 5-30% of the weight of the ezetimibe comprising second layer, polyvinylpyrrolidone as a binder in an amount of 0.5-10% of the weight of the ezetimibe comprising second layer and magnesium stearate in an amount of 0.2-5% of the weight of the ezetimibe comprising second layer.

6. The solid dosage form of claim 4, wherein the rosuvastatin comprising first layer additionally contains butylated hydroxy anisole as an antioxidant in an amount of 0.05-2% of the weight of the first layer and fumed silica as a dispersion agent in an amount of 1-10% of the weight of the first layer.

7. A method of making the solid dosage form of claim 1, the method comprising the steps of:
   a) blending rosuvastatin calcium with pre-gelatinized starch, calcium hydrogen phosphate dihydrate, microcrystalline cellulose and crospovidone to provide a blend, and passing the blend through sieve and lubricating the blend with lubricant to create a rosuvastatin layer blend;
   b) mixing ezetimibe with a wetting agent and a disperse material in isopropyl alcohol and dichloromethane mixture;
   c) absorbing the dispersion of step (b) on lactose and mixing thoroughly; d) air drying the dispersion of step (c), passing it through a sieve, mixing with croscarmellose sodium, and blending;
   e) granulating the mix of step (d) with polyvinylpyrrolidone solution and drying it to obtain ezetimibe granules;
   f) creating bilayer tablet by compressing the blend of step (a) and the granules of step (e) in a bilayer compression machine followed by film coating.

8. The method of claim 7 wherein the lubricant in step a) is sodium stearyl fumarate and the wetting agent in step b) is sodium lauryl sulfate.

9. A method of treating hyperlipidemia, cardiovascular diseases, congestive heart failure, myocardial infarction, or atherosclerosis, the method comprising administering orally the solid dosage form of claim 1 to a patient in need of such treatment.

\* \* \* \* \*